US00PP10823P

United States Patent [19]

Cornelis

[11] Patent Number: Plant 10,823

[45] Date of Patent: Mar. 9, 1999

[54] SPATHIPHYLLUM PLANT NAMED 'ALFA CD'

[75] Inventor: Daniel Cornelis, Melsen, Belgium

[73] Assignee: Reginald Deroose, Evergem, Belgium

[21] Appl. No.: 876,392

[22] Filed: Jun. 16, 1997

[51] Int. Cl.[6] ..... A01H 5/00

[52] U.S. Cl. ..... Plt./88.1

[58] Field of Search ..... Plt./88.1

*Primary Examiner*—Howard J. Locker
*Assistant Examiner*—Melissa L. Kimball
*Attorney, Agent, or Firm*—Foley & Lardner

[57] ABSTRACT

A new and distinct Spathiphyllum plant named 'Alfa CD', characterized by its medium size with relatively large dark green leaves, bushy growth habit which produces many sideshoots, early blossoming period of 24 weeks, suitability for growth in 14–17 cm pots, and its leaves which are slightly toothed at the margins.

1 Drawing Sheet

The present invention comprises a new and distinct cultivar of spathiphyllum, botanically known as *Spathiphyllum hybrid,* and hereinafter referred to by the cultivar name 'Alfa CD'.

The new cultivar is the result of a controlled breeding program carried out by the inventor Daniel Cornelis in Melle, Belgium. The new cultivar was originated from a cross made in 1991 from such program. The male parent was S. 'Pallas' (not patented) and the female parent was S. 'Daniel' (U.S. Plant Pat. No. 8,655). The new cultivar 'Alfa CD' was selected as a flowering plant from the progeny of the stated cross in 1992 in Melle, Belgium by the inventor.

Subsequent asexual reproduction by tissue culture, first performed in 1992 in Evergem, Belgium under the supervision of the inventor, has demonstrated that the combination of characteristics as herein disclosed for the new cultivar are firmly fixed and are retained through successive generations of asexual reproduction.

The following traits have been repeatedly observed and in combination distinguish 'Alfa CD' as a new and distinct cultivar:

1. 'Alfa CD' is a medium size spathiphyllum with rather large leaves.
2. 'Alfa CD' is a bushy plant which produces many sideshoots.
3. The plant blooms after 24 weeks.
4. The leaves are dark green in color and slightly toothed at the margins.
5. Suitable for growth in 14–17 cm pots.

The following observations, measurements and values describe plants grown in Melle, Belgium under greenhouse conditions which closely approximate those generally used in horticultural practice. Color references are made to The Royal Horticultural Society (R.H.S.) Colour Chart, except where general color terms of ordinary significance are used. The color values were determined between 10 AM and Noon in September 1996 under slightly clouded but bright daylight conditions at Melle, Belgium.

The accompanying color photograph shows in front view the unique features of the new cultivar. The colors are as accurate as possible with color illustrations of this type.

Classification: *Spathiphyllum hybrid* cv. 'Alfa CD'.

Parentage:

*Male parent.*—S. 'Pallas'.

*Female parent.*—S. 'Daniel'.

Propagation: Vegetatively propagated by tissue culture.

Plant: A mature plant is 70 cm tall, inclusive of flowers, when grown in a 17 cm pot measured from the bottom of the plant, and approximately 50 cm in diameter, when fully grown. Without flowers the plant is approximately 50 cm tall.

Leaves:

*Form and size.*—Elliptic, nearly symmetrical. Length: 27 to 30 cm. Width : 12 to 13 cm.

*Texture.*—Leathery, upper surface glossy.

*Veins.*—Medium bulging between veins.

*Color.*—Upper surface: Darker than 137 A. Lower surface: 137 C.

*Leaf petiole.*—Length: 25 to 30 cm. Width: 0.5 to 0.7 cm.

*Petiole wings.*—Widest width: 1 cm. Distance between top of the wings and base of the leaf: 3 cm.

Inflorescence:

*Buds.*—Formed in axils of leaves.

*Spathe.*—Color: 155 B. Size: Length : 20 cm. Width : 10 cm. Location to the flower stem: Generally parallel. Shape: Oval, slightly asymmetrical. Flowering time: Flowers repeatedly. First flower appears after 24 weeks. The flowers last for four weeks. Flower stem: Length: 45 cm starting from the sheath of the leaf. Width: 0.6 cm. Total length of the flower and the flower stem: 65 to 70 cm. Angle of the flower stem relative to the leaf base: 35 to 40°. Fragrance: Light.

*Spadix.*—Size: 7 cm in length. Color: 158 B. Longevity: 4 weeks. Position relative to spathe: At approximately midway of its length, the spadix is spaced 1 cm from spathe and generally parallel to the spathe at the midpoint of the spathe.

Reproductive organs:

*Stamens.*—White.

*Anthers and filaments.*—White.

*Pollen.*—White.

*Pistils.*—White.

Roots: White, fleshy roots.

Disease resistance: No known disease resistance.

I claim:

1. A new and distinct cultivar of Spathiphyllum plant named 'Alfa CD', as illustrated and described.

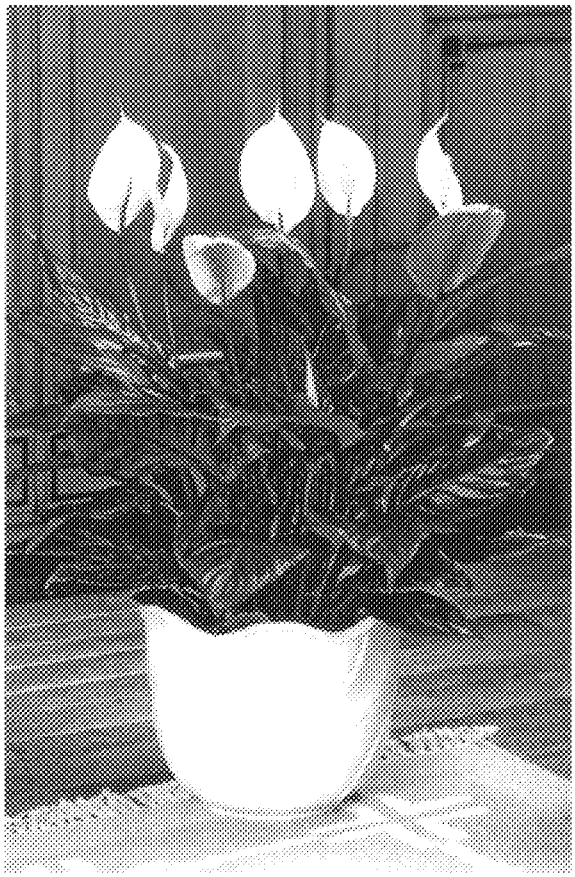

* * * * *